United States Patent
Lane et al.

(10) Patent No.: US 6,221,589 B1
(45) Date of Patent: Apr. 24, 2001

(54) METHODS AND COMPOSITIONS FOR MODULATING MELTING TEMPERATURES OF NUCLEIC ACIDS

(75) Inventors: Michael J. Lane, Baldwinsville, NY (US); Albert S. Benight, Schaumburg, IL (US); Brian D. Faldasz, Maynard, MA (US)

(73) Assignee: TM Technologies, Inc., Woburn, MA (US)

( * ) Notice: Subject to any disclaimer, the term of this patent is extended or adjusted under 35 U.S.C. 154(b) by 0 days.

(21) Appl. No.: 09/116,393

(22) Filed: Jul. 16, 1998

Related U.S. Application Data

(60) Provisional application No. 60/052,845, filed on Jul. 17, 1997.

(51) Int. Cl.[7] ............... C12Q 1/68; C07H 19/00; C07H 21/00; C07H 21/02; C07H 21/04
(52) U.S. Cl. ............... 435/6; 536/22.1; 536/23.1; 536/24.1; 536/24.3; 536/24.31; 536/24.32; 536/25.3; 536/25.32
(58) Field of Search ............... 435/6; 536/22.1, 536/23.1, 24.1, 24.3, 24.31, 24.32, 25.3, 25.32

(56) References Cited

U.S. PATENT DOCUMENTS

| | | | |
|---|---|---|---|
| 4,996,143 | * 2/1991 | Heller et al. | 435/6 |
| 5,446,137 | 8/1995 | Maag et al. | 536/23.1 |
| 5,633,129 | 5/1997 | Karger et al. | 435/6 |

OTHER PUBLICATIONS

Hames et al. Nucleic acid Hybridization, A practical approach pp. 64, 65, and 81, 1985.*

Bell, G.I. et al. "Polymorphic DNA Region Adjacent to the 5' End of the Human Insulin Gene" *Proc. Natl. Acad. Sci. USA* 78(9):5759–5763 (1981).

Dahl, K.S. et al. "Structural Effects on the Circular Dichroism of Ethidium Ion–Nucleic Acid Complexes" *Biochemistry* 21:2730–2737 (1982).

Hahn, F.E. "Distamycin A and Netropsin" *Antibiotics*, (Corcoran, J.W. and Hahn, F.E. eds.), vol. 3, pp. 79–100 (1975).

Marky, L.A. and Breslauer, K.J. "Calculating Thermodynamic Data for Transitions of any Molecularity from Equilibrium Melting Curves" *Biopolymers* 26:1601–1620 (1987).

Southern et al., "Analyzing and comparing nucleic acid sequences by hybridization to arrays of oligonucleotides:evaluation using experimental models," *Genomics*, (1992), vol. 13, pp. 1008–1017.

* cited by examiner

*Primary Examiner*—Jezia Riley
(74) *Attorney, Agent, or Firm*—Lahive & Cockfield, LLP; Giulio A. DeConti; Nicholas P. Triano, III

(57) ABSTRACT

Methods, compositions, and kits for modulating the stability of at least one nucleic acid duplex, are disclosed.

42 Claims, 15 Drawing Sheets

Diminazene Aceturate (Berenil)

Bisbenzimide (Hoechst 33258)

Distamycin A

Actinomycin D

Ethidium Bromide

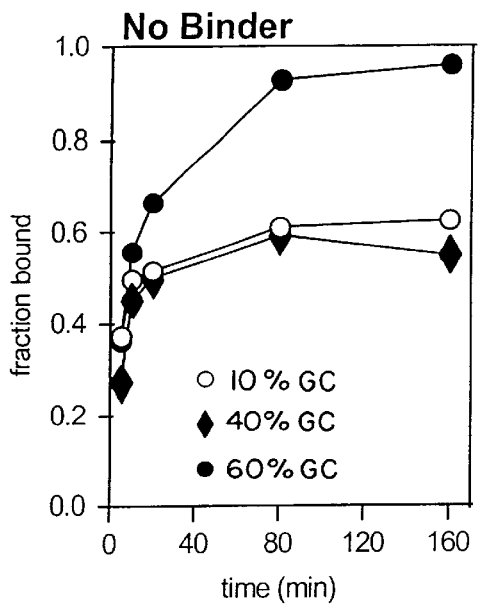
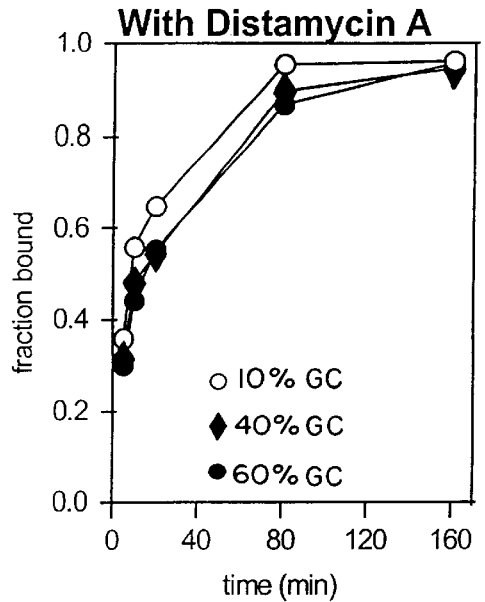
FIG. 9A  FIG. 9B
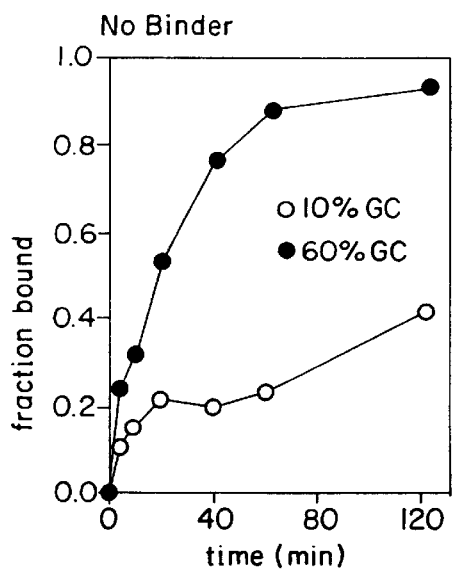
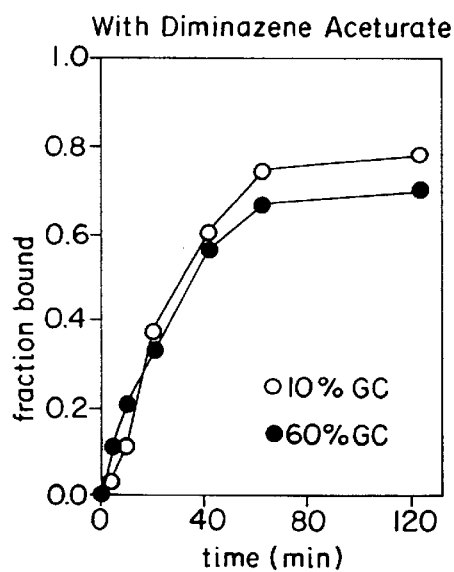
FIG. 10A  FIG. 10B

METHODS AND COMPOSITIONS FOR MODULATING MELTING TEMPERATURES OF NUCLEIC ACIDS

RELATED APPLICATIONS

This application claims the benefit of priority under 35 U.S.C. 119(e) to co-pending U.S. Provisional Application No(s). 60/052,845, filed Jul. 17, 1997, the contents of which is hereby incorporated by reference.

BACKGROUND OF THE INVENTION

The growing demand for sequencing of unknown nucleic acid sequences has spurred the demand for rapid, inexpensive methods of sequencing large amounts of DNA. For example, the Human Genome Initiative will require the sequencing of about 4 billion base pairs of DNA. However, it is possible that current sequencing methodologies, such as Sanger or Maxam-Gilbert sequencing, are not capable of high enough throughput to allow a project of this magnitude to be completed in a reasonable time.

The attention of many researchers has turned to sequencing methods which process sequences in parallel, rather than the serial sequencing methods described above. The promise of parallel "sequencing by hybridization" (SBH) methods is that large amounts of information can potentially be obtained rapidly, in a single experiment. SBH involves the use of multiple probes disposed in an array format to bind to a sample of a target nucleic acid which has been cleaved into smaller fragments. Presently, however, SBH has been attempted on only small DNA targets and with small probe arrays.

Certain problems have arisen in attempts to implement SBH schemes. One serious difficulty is the need to correctly discriminate between target fragments that are perfectly matched to a probe sequence, and target fragments that are bound to a probe sequence despite one or more mismatched bases. This "mismatch discrimination" problem presents the possibility of misidentification of sequences. The problem is especially acute when attempting to differentiate between sequences which bind with significantly different binding energies. For example, in general, AT-rich sequences bind less strongly to their complementary probes than do GC-rich sequences, of the same length, to their respective complementary probes. Thus, it can be difficult to distinguish between perfectly-bound AT-rich sequences and partially mismatched GC-rich sequences. In view of these difficulties, hybridization of mismatched sequences is undesirable, as it makes the unambiguous determination of the target sequence harder to achieve.

SUMMARY OF THE INVENTION

This invention features methods of normalizing the melting temperatures of a plurality of nucleic acid duplexes.

In one aspect, the invention provides a method of normalizing the melting temperatures of at least two nucleic acid duplexes. The method includes the steps of contacting the at least two nucleic acid duplexes with a reaction mixture comprising a nucleic acid binding ligand which preferentially binds to one of the at least two nucleic acid duplexes; such that the melting temperatures of the at least two nucleic acid duplexes are normalized. In a preferred embodiment, a plurality of nucleic acid duplexes are provided in an array, e.g., a 96 well microtiter plate or a high density nucleic acid array, e.g., "gene chip", such that modulating the stability of at least one of the nucleic acid duplexes in the array is effected by forming a reaction mixture comprising the plurality of nucleic acid duplexes and at least one base-preferring nucleic acid binding ligand.

In preferred embodiments, the nucleic acid binding ligand is a duplex-binding ligand. In preferred embodiments, the duplex-binding ligand is distamycin. In preferred embodiments, the reaction mixture comprises at least two nucleic acid binding ligands, and wherein each of the at least two nucleic acid binding ligands independently binds preferentially to one of the at least two nucleic acid duplexes. In preferred embodiments, the reaction mixture comprises at least two duplex-binding ligands. In preferred embodiments, at least one of the at least two nucleic acid binding ligands is a single-strand-binding ligand. In certain embodiments, the reaction mixture further comprises at least one nonspecific nucleic acid binding ligand. In certain embodiments, the reaction mixture further comprises a duplex denaturant, such as, e.g., urea.

BRIEF DESCRIPTION OF THE DRAWINGS

FIG. 9 shows the effect of distamycin A on the association rates of the three sets of target/hairpin molecules, as set forth in Example 6.

FIG. 10 shows the effect of berenil on the association rates of two sets of target/hairpin molecules, as set forth in Example 6.

DETAILED DESCRIPTION OF THE INVENTION

Figure 1A:
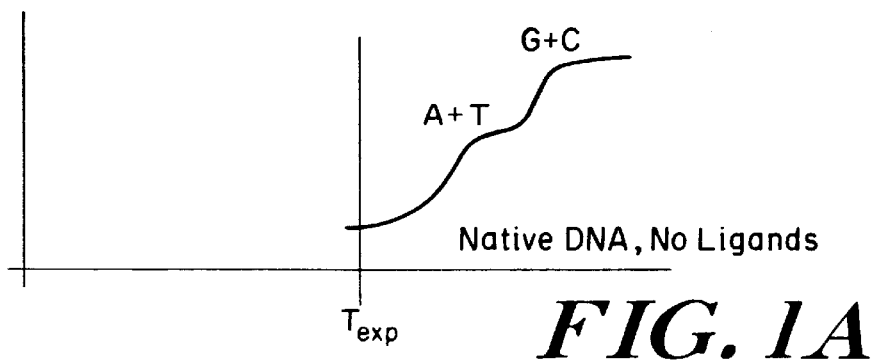
FIGS. 1A–1D show theoretical melting curves of a random mixture of nucleic acid duplexes in the presence of various nucleic acid binding ligands.

The methods and compositions of the invention allow the melting temperatures of a plurality of nucleic acid duplexes to be normalized. By normalizing the melting temperatures of duplexes, the sequence-dependent differences in binding to a probe are eliminated. Thus, the invention provides methods and compositions suitable for improved SBH experiments.

The term "melting temperature", denoted "Tm", as used herein, refers to the midpoint of the duplex-to-single-strand melting transition of a duplex nucleic acid. The Tm of a duplex can be measured by methods well known in the art, some of which are described infra.

The term "normalizing", as used herein, means the process of causing the Tms of a plurality of duplexes to approach a common temperature. In other words, the Tms of a plurality of duplexes are said to be "normalized" if the Tms of the "normalized" duplexes are more nearly the same, in relative or absolute terms, than the Tms of the same duplexes which have not been normalized. "Modulating" the Tms of two or more duplexes, as used herein, refers to increasing or decreasing the absolute or relative difference in the melting temperature between at least two duplexes.

The term "duplex denaturant", as used herein, refers to an agent that, at some concentration, can cause the denaturation, e.g., the dissociation, of nucleic acid duplexes, either in sequence-specific, base-preferring or non-sequence-specific contexts. Duplex denaturants include any chemical agent that, under suitable conditions, can alter the duplex-single strand equilibrium so as to favor single strand formation and disfavor duplex formation. Increased temperature (heating) can be used instead of a (chemical) duplex denaturant, although this is not preferred. In preferred embodiments, a duplex denaturant is a chemical or biochemical reagent. Exemplary duplex denaturants include enzymes and proteins such as single-strand binding protein (e.g., from *E. coli*), the G-5 protein, the gene 32 protein, Rec A, poly(lysine-phenylalanine), poly(arginine), and helicases, as well as chemical denaturants such as urea or formamide. Duplex denaturants can be identified by measuring the Tm of a duplex in the presence and the absence of a suspected duplex denaturant; a duplex denaturant at some concentration will lower the Tm of the duplex. Preferred duplex denaturants do not have an adverse effect on other components of a reaction mixture, when used in amounts sufficient to destabilize at least one duplex. For example, a duplex denaturant should not inhibit the activity of enzymes, such as polymerase or ligase, if activity of such enzymes is desired.

The term "duplex-binding ligand" as used herein, refers to a reagent which "prefers" binding to duplex nucleic acid substrates rather than single stranded nucleic acids; that is, a duplex-binding ligand binds to a duplex nucleic acid with a greater binding energy than the energy with which the ligand binds to either of the single-strands which make up the duplex. In preferred embodiments, a duplex binding ligand is a chemical or biochemical reagent. Exemplary duplex-binding ligands include enzymes such as polymerases, ligases, and the like; intercalators; drugs such as Berenil (diminazine aceturate), bis-benzamide, ethidium bromide, actinomycin D and distamycin A; and the like. Duplex-binding ligands can be identified by measuring the Tm of a duplex in the presence and the absence of a suspected duplex-binding ligand; a duplex-binding ligand at some concentration will raise the Tm of the duplex. Preferred duplex-binding ligands do not have an adverse effect on other components of a reaction mixture, when used in amounts sufficient to stabilize at least one duplex. For example, in preferred embodiments, a duplex-binding ligand should not inhibit the activity of enzymes, such as polymerase or ligase, if activity of such enzymes is desired.

The term "base-preferring binding ligand", as used herein, refers to a nucleic acid binding ligand that preferentially binds to nucleic acid sequences (or duplexes) in which one or more specified bases predominate. Thus, for example, a nucleic acid binding ligand that preferentially binds to sequences rich in A or T is a base-preferring binding ligand (also referred to as an "AT-binding ligand"). A "base-preferring binding ligand" can be, but need not be, a sequence-specific binding ligand (which is a ligand that preferentially binds to a particular sequence or sequences), nor is a sequence-specific binding ligand necessarily a base-preferring binding ligand, although it can be. For example, a ligand that preferentially binds to a sequence motif of AGCT is sequence specific (for the sequence AGCT), but is not base-preferring because the base composition in the sequence is evenly distributed among A, G,C and T.

The term "nonspecific binding ligand", as used herein, refers to a nucleic acid binding ligand that does not substantially preferentially bind to nucleic acid sequences in which one or more specified bases predominate. That is, a "nonspecific binding ligand" binds to all, or a large variety of, bases or sequences approximately equally well.

The term "modulating the stability" of nucleic acid duplexes, as used herein, refers to the process of changing the stability (either increasing or decreasing) of at least one duplex in a mixture of a plurality of duplexes.

The term "nucleic acid strand", as used herein, refers to a strand of DNA or RNA, or a mixed DNA-RNA strand, or nucleic acid-like compounds such as peptide nucleic acids. A nucleic acid strand can also include modified (e.g., chemically or biochemically modified) DNA or RNA bases, of which many are known in the art.

As used herein, the term "AT-rich" means a sequence (e.g., all or part of a strand or duplex) in which greater than 50% of the nucleic acid bases are A or T. Furthermore, for purposes of the invention, when RNA or chimeric RNA-DNA sequences are used, it will be understood that references to thymidine (T) can also apply to uridine (U), unless indicated otherwise. Similarly, the term "GC-rich" means a sequence (e.g., all or part of a strand or duplex) in which greater than 50% of the nucleic acid bases are G or C.

The term "target nucleic acid sequence" or "target strand" refers to a nucleic acid sequence which is to be detected, sequenced, immobilized, or manipulated. The target nucleic acid sequence can be any nucleic acid strand, as defined above, and in general will be single-stranded or will be made single-stranded by methods known in the art. The target nucleic acid sequence can be obtained from various sources including plasmids, viruses, bacteria, fungi, yeast, plants, and animals, including humans; or the target nucleic acid sequence can be obtained from non-natural sources. The target nucleic acid sequence can be obtained from various organisms or tissues, including fluids such as blood, semen, urine and the like. The target nucleic acid sequence is preferably extracted or purified to remove or reduce contaminating or interfering materials such as proteins or cellular debris. Procedures for such purification or extraction of target nucleic acids sequences are known in the art, including, for example, those described in Maniatis et al., "Molecular Cloning: A Laboratory Manual", Cold Spring Harbor Laboratory (1989), or in Bell et al., *Proc. Nat. Acad. Sci. USA* (1981), 78:5759–5763.

The compositions and methods of the invention generally feature the use of at least one base-preferring binding ligand (or, in some cases, sequence-specific ligand) to modulate or normalize the stability (or melting temperature) or at least one nucleic acid duplex. The methods and compositions of the invention can also include one or more additional binding ligands, which can be base-preferring or sequence-specific ligands, or non-specific ligands, and can bind duplexes or single strands. The choice of appropriate ligands will be routine to the skilled artisan in light of the teachings herein, as explained in more detail below.

Ligands suitable for use in the present invention are capable, in general, of binding to nucleic acid single strands and/or duplexes. In general, it is necessary to provide at least one base-preferring ligand in the reaction mixtures of the invention.

A variety of base-preferring ligands have been described. For example, the duplex-binding ligand Distamycin A has been reported to bind preferentially to AT-rich sequences.

Other base-preferring duplex-binding ligands include certain restriction enzymes, drugs such as actinomycin D (which has a primary binding site of 5'-GC-3', and a secondary preference for GT sites), and intercalators such as ethidium bromide (as described below).

Similarly, base-preferring single strand-binding ligands can be employed in the invention.

Base-preferring binding ligands can be identified by methods known in the art. For example, the effect of a ligand on the Tm of test sequences can be used to determine whether the ligand is a base-preferring binding ligand. For example, an AT-rich duplex can be melted in the absence and presence of a candidate ligand, and a GC-rich duplex similarly melted in the absence and presence of the candidate ligand. A base-preferring duplex-binding ligand that preferentially binds to AT-rich sequences (an "AT-duplex binding ligand") can, at some concentration of the binding ligand, raise the Tm of the AT-rich duplex more than the GC-rich duplex. A duplex-binding ligand that preferentially binds to GC-rich sequences (a "GC-duplex binding ligand") can, at some concentration of the binding ligand, raise the Tm of the GC-rich sequence more than the AT-rich sequence. Similarly, a single strand-binding ligand that preferentially binds to AT-rich strands (a "AT-single strand binding ligand") can, at some concentration of the binding ligand, lower the Tm of an AT-rich duplex more than the Tm of a GC-rich duplex.

In preferred embodiments, a base-preferring binding ligand binds at least n percent more strongly to a preferred strand or duplex than to a nonpreferred strand or duplex, where n is 10, 20, 30, 50, 80, 100, or 150. For example, a preferred AT-duplex-binding ligand can bind at least n percent more strongly to an AT-rich duplex than to a GC-rich duplex. The relative preference of a ligand for a particular base or bases can be measured by techniques known in the art. An exemplary technique for determining binding preference of a ligand is known as "footprinting". In brief, a potential base-preferring binding ligand is incubated with a nucleic acid strand or duplex, and the resulting complex is then incubated with a reagent that modifies the strand or duplex only at sites which do not bind the ligand. An illustrative reagent is a restriction enzyme that cleaves or methylates a nucleic acid strand only at sites where no ligand is bound. By varying the concentration of the binding ligand employed in the footprinting reaction, the relative affinity of the ligand for, e.g., AT-rich sequences and for GC-rich sequences can be determined and compared.

Furthermore, a wide variety of substantially non-base-preferring ligands are known, including duplex-binding ligands such as enzymes (including certain restriction enzymes, polymerases, ligases, and the like); drugs; non-sequence-specific intercalaters; and the like.

In general, the methods of the invention feature the use of reaction mixtures comprising at least one base-preferring binding ligand. The base-preferring binding ligand can be either a single-strand-binding ligand or a duplex-binding ligand. In preferred embodiments, the base-preferring binding ligand is an AT-duplex binding ligand. In other preferred embodiments, the base-preferring binding ligand is a GC-single strand binding ligand.

The methods of the invention can also employ more than one binding ligand, provided that at least one is a base-preferring binding ligand. Thus, for example, a reaction mixture comprising a base-preferring duplex-binding ligand and a base-preferring single-strand-binding ligand can be employed in the methods of the invention. A reaction mixture comprising, for example, a base-preferring single-strand-binding ligand and a (nonspecific) duplex denaturant, can also be employed in the invention.

The invention provides methods of modulating the stability (e.g., the Tm) of a plurality of duplexes. As shown in the Examples, infra, base-preferring binding ligands can be employed to either decrease or increase the differences in melting temperature between AT-rich and GC-rich duplexes. Thus, methods of the invention are useful when it is desirable to attenuate or decrease the differences in binding energy between disparate sequences (for example, in sequencing by hybridization experiments), or when it is desirable that the differences in binding energy be increased (for example, to increase stringency and decrease hybridization of mismatched sequences). These techniques may be employed in arrays such as gene chips, for e.g., high-density hybridization which are within the scope of the present invention.

Accordingly, the methods of the invention are useful in a wide variety of nucleic acid hybridization experiments in which it is desirable to modulate the melting temperatures of a plurality of nucleic acid sequences. Illustrative examples of experiments in which the methods of the invention find use include SBH, detection of target nucleic acids (e.g., assays), and the like. By way of non-limiting example, one application of the invention may be where it is desired to characterize and/or sequence a population of single-stranded DNA target sequences, e.g., 40 mers, from a mixture. An array comprising bound capture moieties each having determined but differing sequences, such as described in U.S. Pat. No. 5,770,365, is provided. (The array may comprise, on the one hand, a microtiter plate having 96 positions in the array, to a "gene chip" having 96,000 positions, on the other.) Aliquots of the nucleic acid mixture of interest are placed in each array position so as to contact the capture moieties in each array under conditions favorable for hybridization, and the melting temperatures are normalized as described herein. After washing the array to remove unbound or mismatched DNA (a step which may include treatment with duplex denaturant as described herein), the bound DNA segments may be detected, sequenced, immobilized, or manipulated, etc. as known in the art.

In one embodiment, the invention provides a method for normalizing the melting temperatures of at least two nucleic acid duplexes. The method includes the step of contacting the at least two nucleic acid duplexes with a reaction mixture comprising a base-preferring nucleic acid binding ligand; such that the melting temperatures of the at least two nucleic acid duplexes are normalized. In preferred embodiments, the base-preferring nucleic acid binding ligand is a duplex-binding ligand, such as distamycin. In certain embodiments, the reaction mixture comprises at least two base-preferring nucleic acid binding ligands, which can be at least two duplex-binding ligands. In certain embodiments, the base-preferring nucleic acid binding ligand is a single-strandbinding ligand. In certain embodiments, the reaction mixture further comprises at least one nonspecific nucleic acid binding ligand. In certain embodiments, the reaction mixture further comprises a duplex denaturant, for example, urea.

The melting temperatures of at least two nucleic acid duplexes can be normalized (by a pre-selected amount) by addition of a sufficient amount of an appropriate binding ligand or ligands, as described herein. In certain preferred embodiments, the melting temperatures of the at least two nucleic acid duplexes are substantially completely normalized, i.e., the melting temperatures are made substantially equal. In other preferred embodiments, the melting temperatures are adjusted so that the difference between the melting temperatures of the duplexes after normalization is at least 10%, 20%, 30%, 50%, 70%, 80%, or 90% less than the difference between the melting temperatures of the duplexes prior to normalization according to the methods of the invention.

The amount of binding ligand necessary to effect a desired degree of normalization can be determined by titration of the binding ligand or ligands into the mixture of duplex nucleic acids and determination of the melting temperatures of the duplexes over a range of ligand concentrations. It will be appreciated that combinations of ligands can, in certain cases, provide greater normalization of melting temperatures than a single binding ligand alone. For example, addition of an AT-preferring duplex binding ligand will tend to stabilize the formation of AT-rich duplexes, and raise the melting temperature of AT-rich duplexes. Addition of a GC-preferring binding ligand will tend to stabilize GC-rich single strands, which results in destabilization of GC-rich duplexes, generally lowering the melting temperature of GC-rich duplexes. Thus, combination of an AT-preferring duplex binding ligand with a GC-preferring single-strand binding ligand can result an increase in melting temperature of AT-rich sequences, and a decrease in the melting temperature of GC-rich sequences. In the common situation in which an AT-rich duplex has a lower melting temperature (in the absence of ligands) than a GC-rich duplex of the same length, the combination of an AT-preferring duplex binding ligand with a GC-preferring single-strand binding ligand can normalize the melting temperatures of GC-rich sequences and AT-rich sequences by acting on both types of sequence.

In another embodiment, the invention provides a method for modulating the stability of a plurality of nucleic acid duplexes. The method includes the steps of i) providing a plurality of duplexes; and (ii) forming a reaction mixture comprising the plurality of duplexes and a base-preferring nucleic acid binding ligand; such that the stability of at least one duplex is modulated. In preferred embodiments, the base-preferring binding ligand is a duplex-binding ligand. In certain embodiments, the reaction mixture further comprises a single-strand-binding ligand.

In another aspect, the invention provides a buffer for modulating the melting temperatures (e.g., normalizing the melting temperatures) of at least one, more preferably at least two, nucleic acid duplexes. The buffer includes at least one base-preferring (or sequence-specific) nucleic acid binding ligand in an amount sufficient to modulate the melting temperature of at least. In preferred embodiments, the buffer includes at least two nucleic acid binding ligands (which can be base-specific or sequence-specific). The buffer can also include a duplex denaturant; a single-strand binding nucleic acid binding ligand; a duplex-binding ligand; and/or a nonspecific ligand.

In still another aspect, the invention provides kits for modulating (e.g., normalizing) the melting temperature of at least one, more preferably at least two, nucleic acid duplexes. The kit includes a container of a nucleic acid binding ligand, which can be a base-preferring or a sequence specific binding ligand. In preferred embodiments, the kit includes at least two nucleic acid binding ligands (which can be base-specific or sequence-specific). The kit can also include a duplex denaturant; a single-strand binding nucleic acid binding ligand; a duplex-binding ligand; and/or a nonspecific ligand.

The invention is further illustrated by the following Exemplification, which should not be construed as further limiting the subject invention.

EXEMPLIFICATION

General Methods

Partially complementary DNA hairpins were synthesized by standard methods on a DNA synthesizer. The hairpins had the following structure: 5'-ACGGC CTTTC TATAG ($N_{10}$) GAATT CGGCG TACTC GACCG GACTT TTGTC CGGTC GAGTA CGCCG AATTC ($N'_{10}$) CTATA GAAAG GCCGT-3' The notation $N_{10}$ indicates a 10-bp region of random sequence, which was synthesized by programming the DNA synthesizer to use all 4 bases (i.e., A, G, C, T) for these positions; $N'_{10}$ denotes the complement of $N_{10}$. The hairpins had a 48-base pair duplex stem (a self-complementary region 48-bp in length) linked by a -T-T-T-T- loop.

The hairpins were synthesized by synthesizing precursor molecules (made by standard phosphoramidite chemistry on an ABI 380B synthesizer) having the structure: 5'-ACGGC CTTTC TATAG ($N_{10}$) GAATT CGGCG TACTC GACCG GACTT TTGTC CGGTC GAG-3' After synthesis, the precursor molecules were purified by HPLC, detritylated, dialyzed, and lyophilized. The precursor molecules were extended to the full hairpins by incubation with DNA polymerase or reverse transcriptase. For example, 100 µg of the precursor molecules were dissolved in buffer (120 mM Tris-HCl (pH 8.3), 150 mM KCl, 10 mM $MgCl_2$,1 mM dithiothreitol, 10 mM each of dGTP, dATP, dCTP, and dTTP). Approximately 10–12 units of AMV reverse transcriptase (Promega) was added to a volume of 25 µl. The sample was incubated for five hours, and then the extended hairpins were separated from unreacted molecules by polyacrylamide gel electrophoresis (PAGE). Other DNA polymerases such as Large Klenow fragment (New England Biolabs) can be substituted for reverse transcriptase.

Figure 1B:
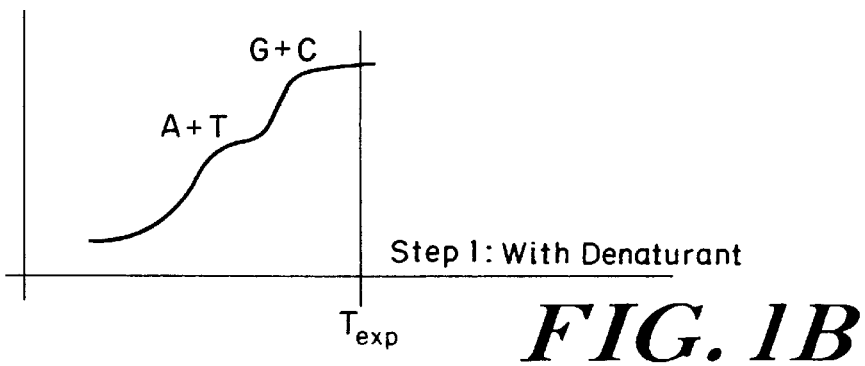
Figure 1C:
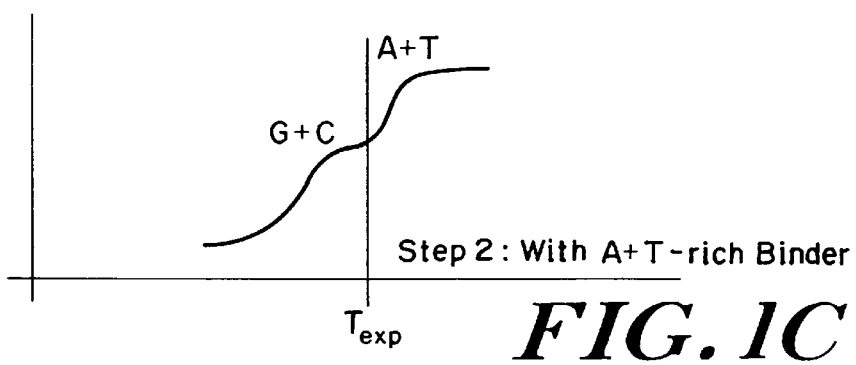
Figure 1D:
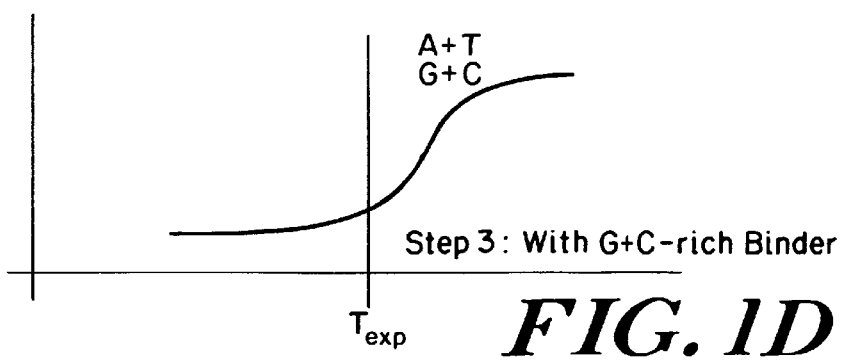

The hairpins synthesized as described above represent a statistical mixture of the 410 possible hairpins with a 10-bp random sequence within the 48-bp duplex ("stem") region, and a 4-bp loop. The hairpin structure was chosen for these experiments to assure unimolecular melting transitions and avoid concentration dependence of melting (see, e.g., L. A. Marky and K. J. Breslauer, *Biopolymers* 26:1601–1620 (1987)). The random mixture of duplex structures results in a melting curve that is a composite of the individual melting curves. The Tm of the most GC-rich hairpins will in general be higher than the Tm of AT-rich sequences, so the composite melting curve can have multiple transitions due to the different melting temperatures (see FIG. 1A for a theoretical depiction of this melting behavior). This mixture of DNA hairpins was used in the Examples described below. FIGS. 1B–1D show idealized melting behavior of a random mixture of duplexes in the presence of various binders of DNA. FIG. 1B shows the decrease in melting temperature of duplexes in the presence of a non-specific duplex denaturant (compared to the control). FIG. 1C shows the increase in melting temperature of AT-rich ("A+T") regions upon addition of an AT-binding duplex binding ligand to the reaction mixture of FIG. 1A; melting temperatures are lower than the control (FIG. 1A due to the presence of the denaturant). FIG. 1D shows the effect of addition of a GC-specific duplex binding ligand to the reaction mixture of FIG. 1C; the melting temperature of GC-rich ("G+C") regions has increase compared to the melting curve of FIG. 1C.

The melting experiments described in Examples 1–4 were conducted by monitoring the absorbance of a sample solution at 268 nm, as is known in the art. Each sample consisted of about 0.5 $\mu$M DNA hairpins (having an optical density of about 0.5) in 1 ml of buffer (10 mM cacodylate, pH 7.9 at 25° C.; 2 mM $MgCl_2$; 100 mM NaCl). Additives were included where indicated (urea, Distamycin A, ethidium bromide (denoted as eth Br in the Figures)). The solution was placed in a 1 cm pathlength semi-micro quartz cuvette and monitored by a Hewlett-Packard 8452A diode-array spectrophotometer equipped with a temperature-controlled cell holder. Temperatures were increased from 24° C. to 100° C. at a rate of 1 ° C. per minute. The curves of absorbance vs. temperature were normalized to upper and lower baselines and smoothed using a digital filter. Derivative curves were used to observe the fine structure of melting transitions. The melting temperature Tm was taken as the temperature at the midpoint of the melting transition (that is, where 50% of the duplexes had melted).

As previously mentioned, Distamycin A is a duplex-binding ligand that is a minor-groove binder with a preference for AT-rich sequences (see, e.g., F. E. Hahn in "Antibiotics", v. 3, J. W. Corcoran and F. E. Hahn, Eds., Springer-Verlag, New York (1975), pp. 79–100).

Ethidium bromide, although often considered to be a nonspecific duplex binder (intercalator), exhibits a preference for sequences in the order d(CpG)>d(CpA)>d(TpA)>d(ApA)>d(ApG)>d(ApT) (see, e.g., Dahl et al., *Biochemistry* 21:2730–2737 (1982)).

EXAMPLE 1

Figure 2A:
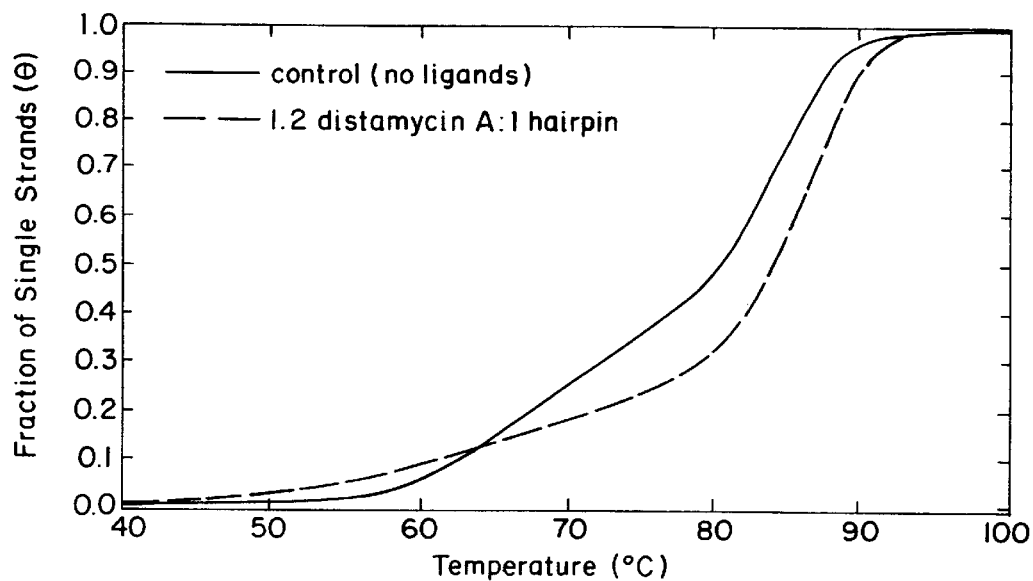
FIG. 2A shows experimental melting curves of a DNA hairpin duplex in the absence and presence of Distamycin A.
Figure 2B:
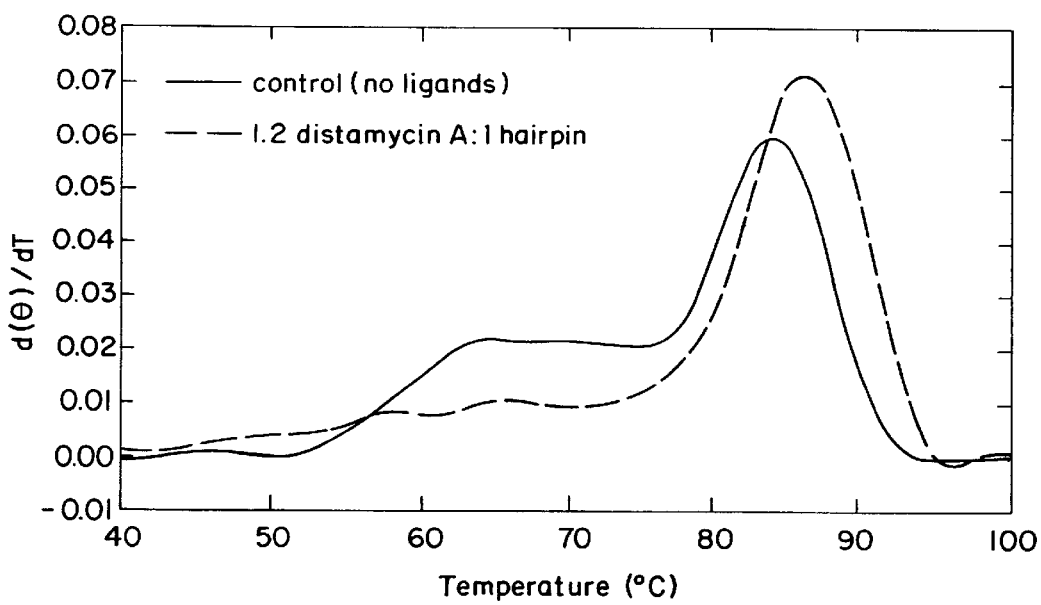
FIG. 2B plots the derivative of the curve in FIG. 2A.

The experimental melting curve of the mixture of DNA hairpins, in the absence of binding ligands (control), is shown in FIG. 2A (solid line). As expected, the melting transitions occur over a range of temperature, leading to several regions of melting and a broad melting range. The derivative of the melting curve shows the broad transition more clearly (FIG. 2B, solid line). The addition of Distamycin A (in a 1.2:1 mole ratio with the DNA hairpins) causes a significant change in the shape of the melting curves (FIGS. 2A and 2B, dashed lines). The addition of the AT-binding ligand Distamycin A causes the melting curve to shift to higher temperatures compared to the control melting curve (FIG. 2A); the difference in Tm is about 4° C. In FIG. 2B, it can be seen that the transition to higher melting temperature has resulted in a decrease in melting in the lower temperature region (e.g., between about 60° C. and 77° C.), where the AT-rich sequences would be expected to melt. Thus, the AT-rich sequences, which melted at lower temperatures in the absence of the binding ligand, appear to melt at higher Tm in the presence of the AT-binding ligand. Also, the derivative curve has changed in shape, not simply shifted position along the temperature axis. The shape of the derivative melting curve, with a decrease in the rate of melting at lower temperatures and an increase at higher temperatures, suggests that the melting of the AT-rich sequences has been shifted to the high-temperature region, while the Tm of the GC-rich sequences has not been shifted as much.

This experiment demonstrates that the addition of an AT-duplex-binding ligand can modulate the melting temperature of AT-rich sequences, shifting the Tm to higher temperatures. Furthermore, the Tm of AT-rich sequences is shifted to a greater extent than is the Tm of GC-rich sequences. Thus, the melting temperatures of disparate sequence have been at least partially normalized, i.e., the difference in melting temperatures between AT-rich duplexes and GC-rich duplexes is generally reduced.

EXAMPLE 2

Figure 3A:
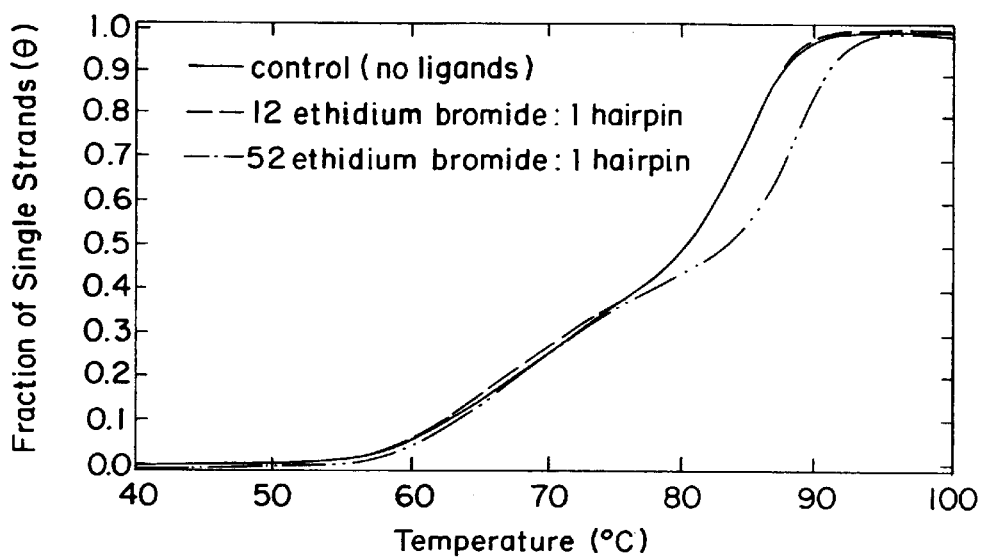
FIG. 3A shows experimental melting curves of a DNA hairpin duplex in the absence and presence of ethidium bromide.
Figure 3B:
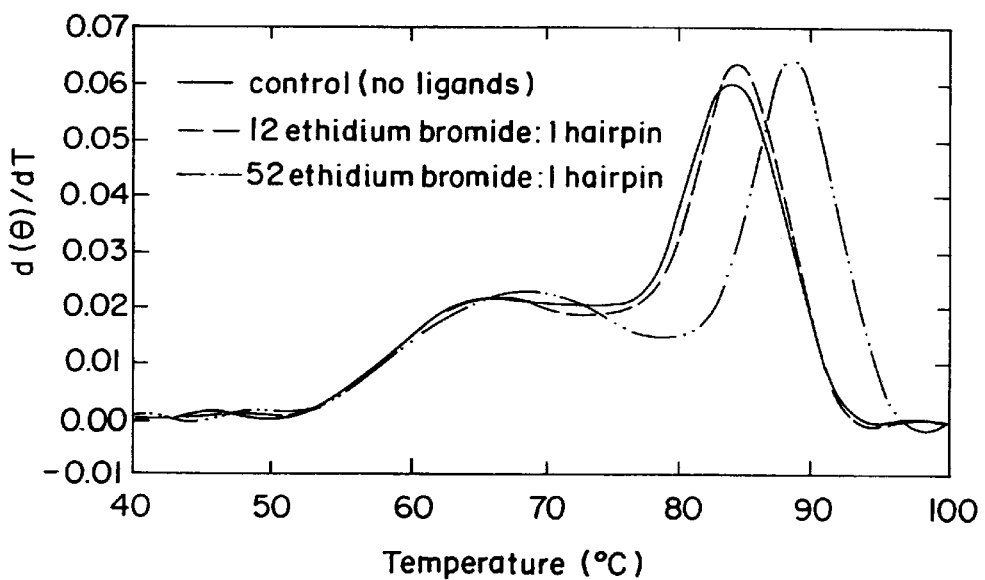
FIG. 3B plots the derivative of the curves in FIG. 3A.

The melting of DNA hairpins in the presence and absence of ethidium bromide, a GC-duplex binding ligand, is shown in FIGS. 3A and 3B. In FIG. 3A, the melting of DNA hairpins without added ethidium bromide is shown by the solid curve. Addition of ethidium bromide in a 12:1 molar ratio (ethidium bromide:hairpin) results in only a slight change in melting behavior (dashed curve). However, addition of ethidium bromide in a 52:1 molar ration results in a significant shift (dotted and dashed curve). As seen in the derivative curves shown in FIG. 3B, at a ratio of 52:1, ethidium bromide causes an overall increase in the Tm of the mixture (by about 3.5° C.). In contrast to the melting result shown in Example 1, however, the melting behavior in the lower temperature region (e.g., between about 60° C. and 75° C.) has changed very little, whereas the higher temperature region has shifted sharply to higher temperature. The derivative curve shows that the melting transitions have separated into two distinct regions, a low-temperature region where the AT-rich sequences melt, and a high-temperature region where the GC-rich sequences melt.

This experiment shows that the addition of a GC-duplex binder can modulate the melting temperature of a plurality of duplexes by shifting the Tm of GC-rich sequences to higher temperatures while leaving the melting temperatures of AT-rich sequences substantially unchanged. The effect is to further accentuate the differences in melting temperature between AT-rich sequences and GC-rich sequences.

Example 3

The combination of a base-preferring duplex-binding ligand and a duplex denaturant was tested in a melting experiment performed according to the following general procedure.

Figure 4A:
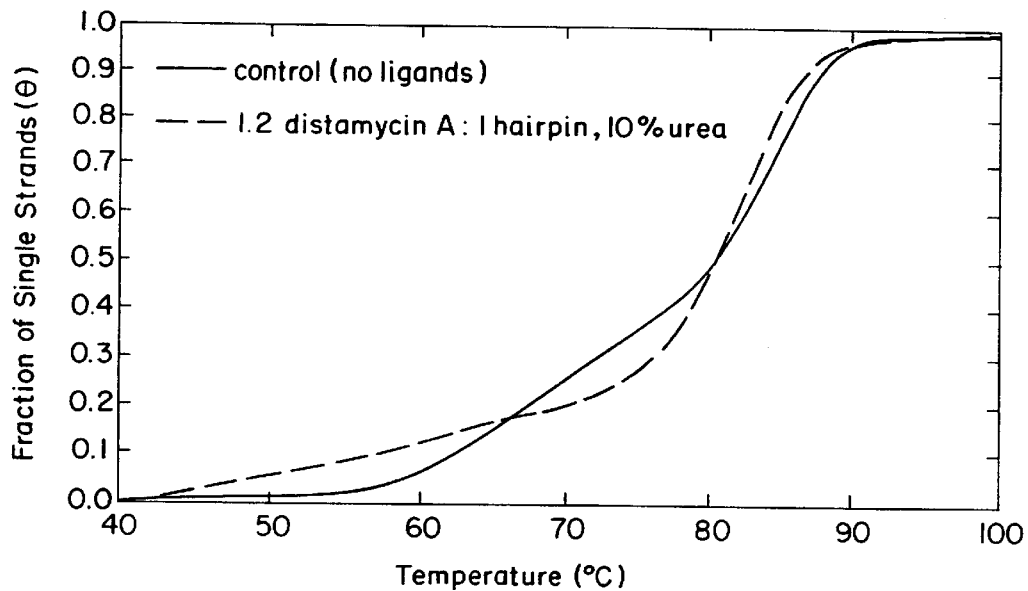
FIG. 4A shows experimental melting curves of a DNA hairpin duplex in the absence and presence of Distamycin A and urea.
Figure 4B:
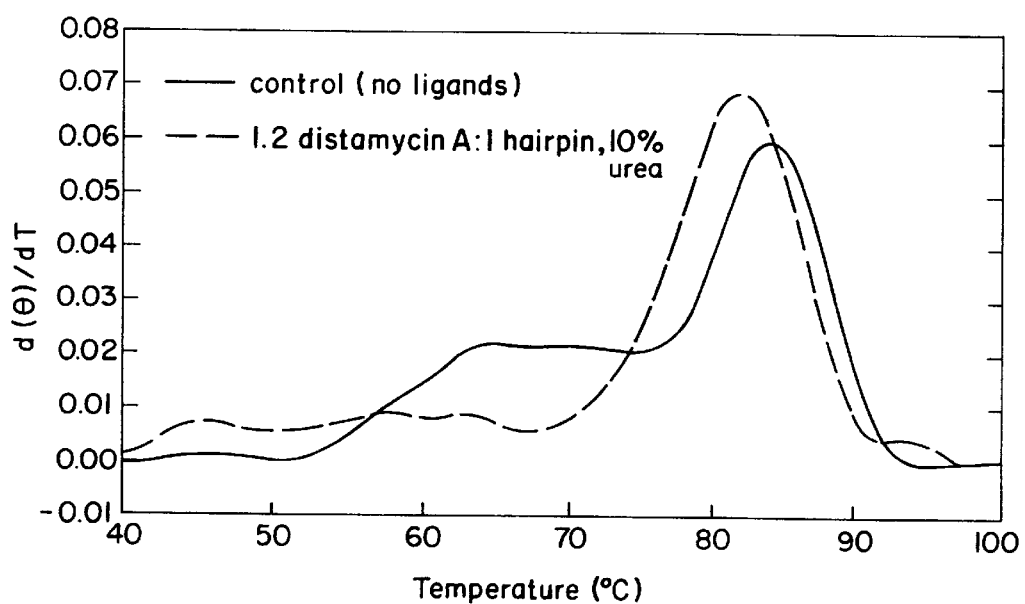
FIG. 4B plots the derivative of the curves in FIG. 4A.

The melting profile of DNA hairpins in the absence (solid lines, FIGS. 4A and 4B) and presence (dashed lines) of Distamycin A and urea shows the combined effects an AT-duplex binding ligand and a duplex denaturant. Distamycin A was present in a 1.2:1 molar ratio to DNA hairpins; urea was present at a concentration of 10% (w/v) in the melting buffer. Compared to the melting profile of the hairpins in the presence of Distamycin A alone (FIG. 2, Example 1), the overall Tm of the duplexes has decreased; compared to the control, the Tm is almost unchanged. Thus, the added duplex denaturant urea lowers the overall Tm of the duplexes, as expected. It is also clear that the distribution of melting temperatures has been altered compared to the control; the melting transitions at lower temperatures (e.g., in the range between about 60 and 75° C.) appear to have been shifted to higher temperature.

This experiment demonstrates that added duplex denaturants lower the Tm of duplexes. Urea in particular appears to be a substantially nonspecific duplex denaturant.

Example 4

Figure 5A:
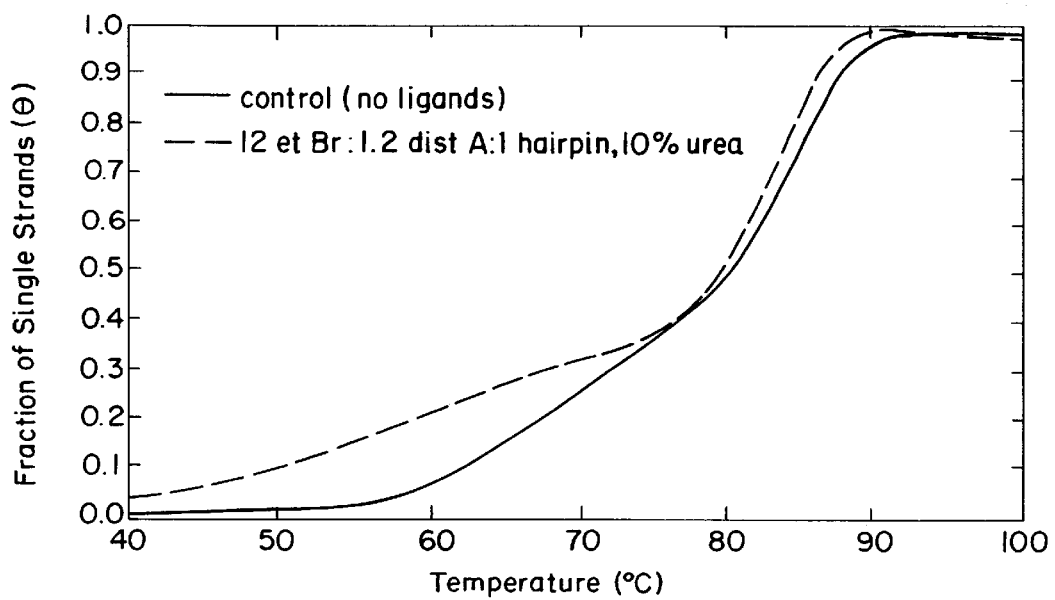
FIG. 5A shows experimental melting curves of a DNA hairpin duplex in the absence and presence of ethidium bromide, Distamycin A, and urea.
Figure 5B:
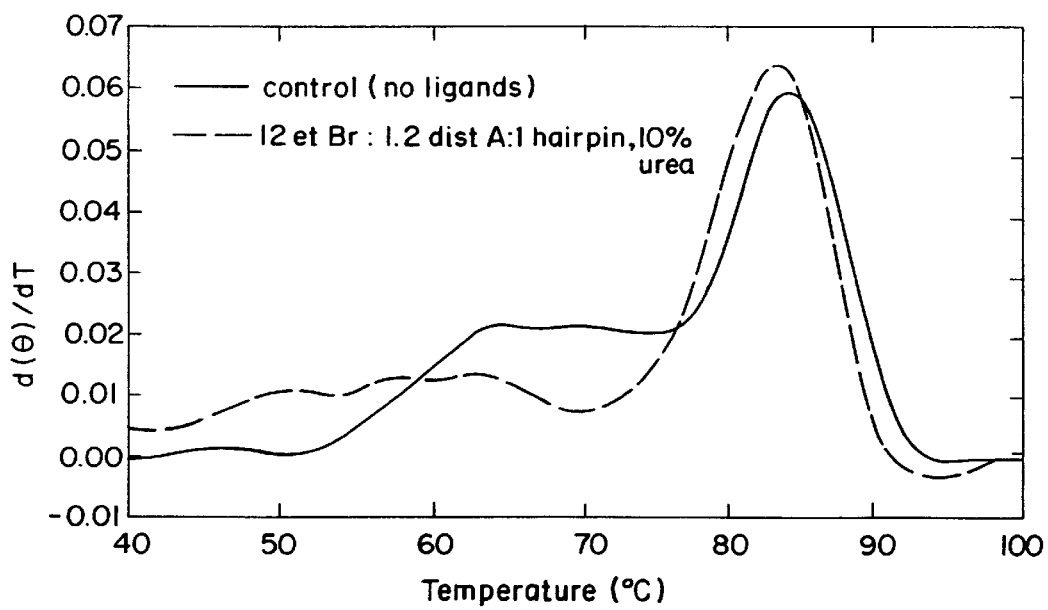
FIG. 5B plots the derivative of the curves in FIG. 5A.
Figure 6A:
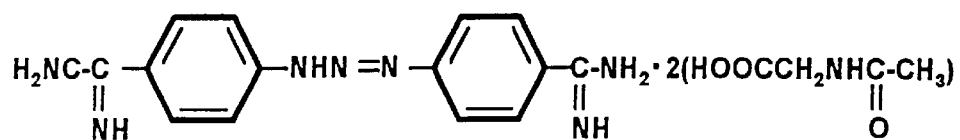
FIG. 6 shows the chemical structures of certain duplex binding ligands.
Figure 6B:
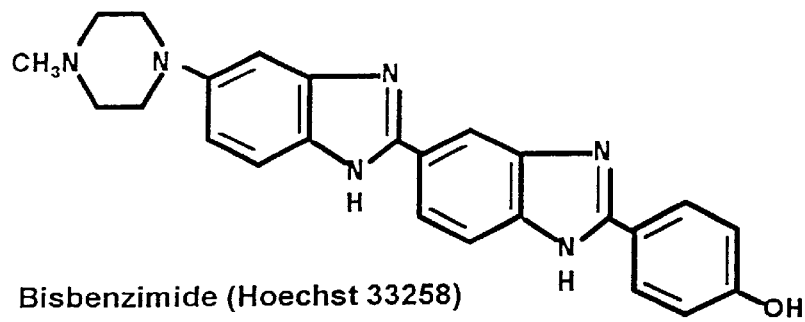
Figure 6C:
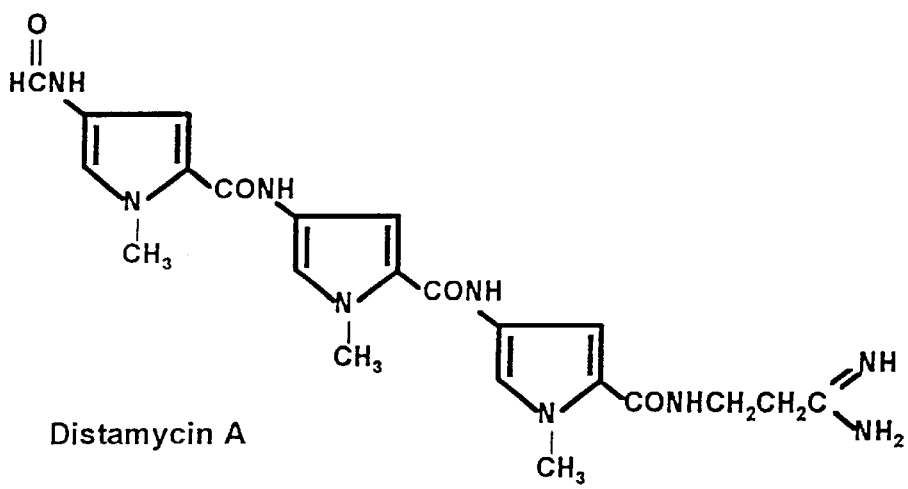
Figure 6D:
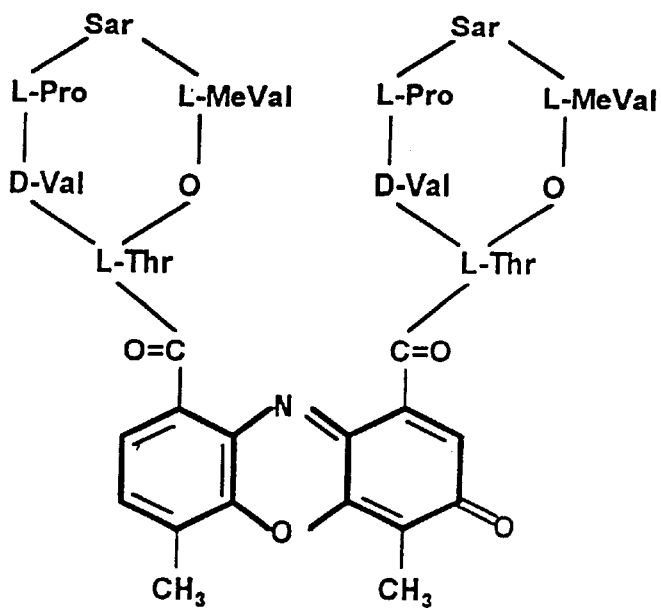
Figure 6E:
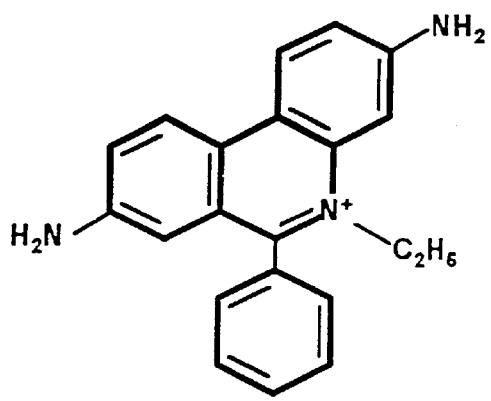
Figure 7A:
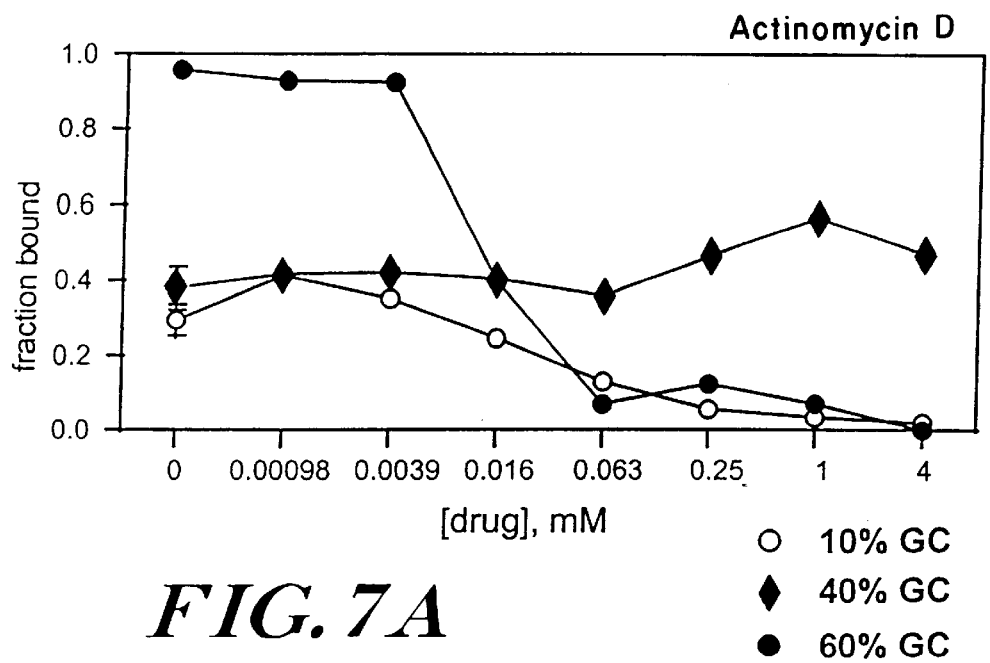
FIG. 7 shows the results of titration of the hairpin/target sets with various duplex binding ligands as shown in Example 5.
Figure 7B:
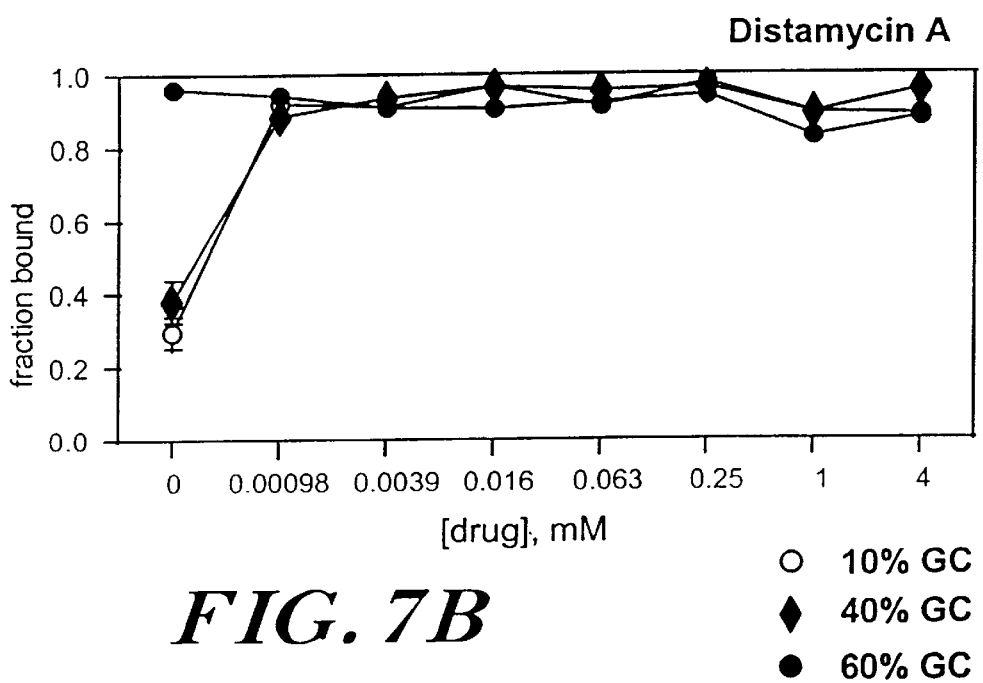
Figure 7C:
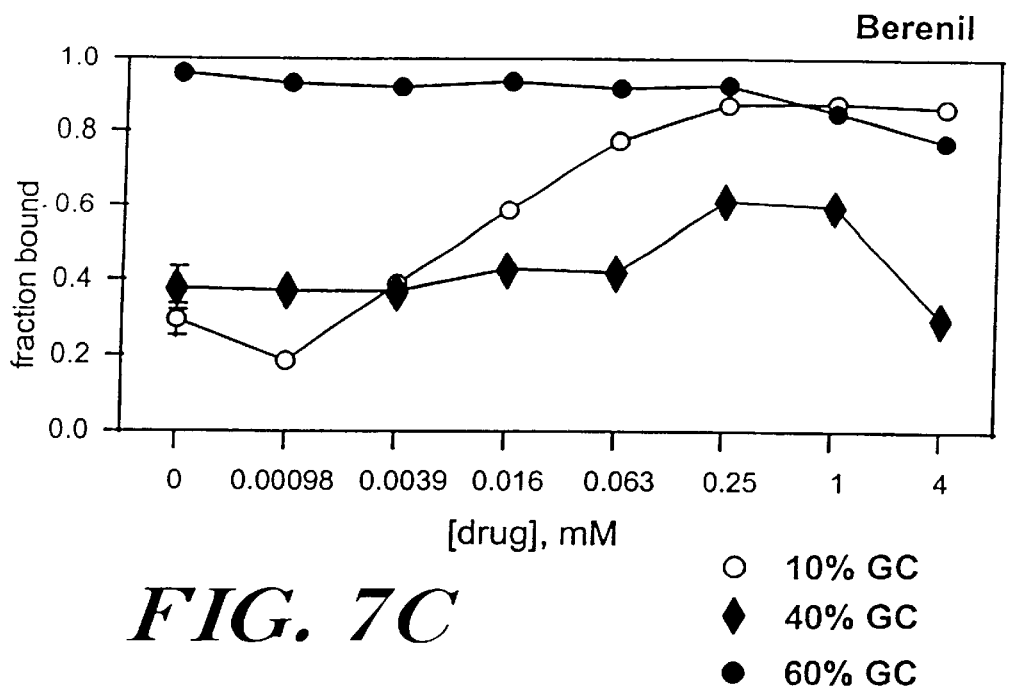
Figure 7D:
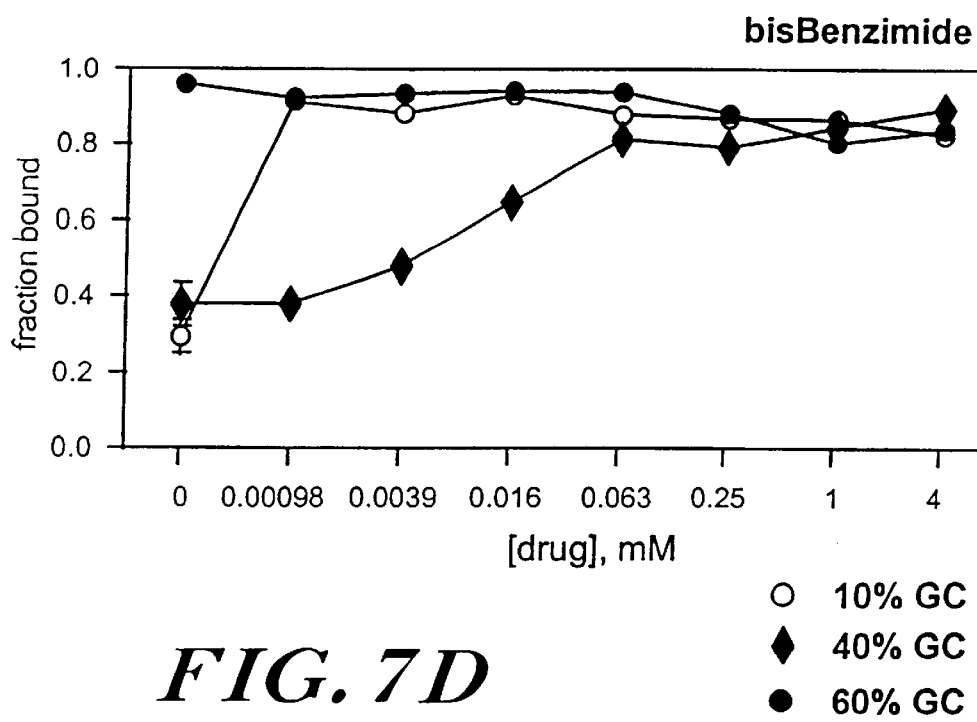
Figure 7E:
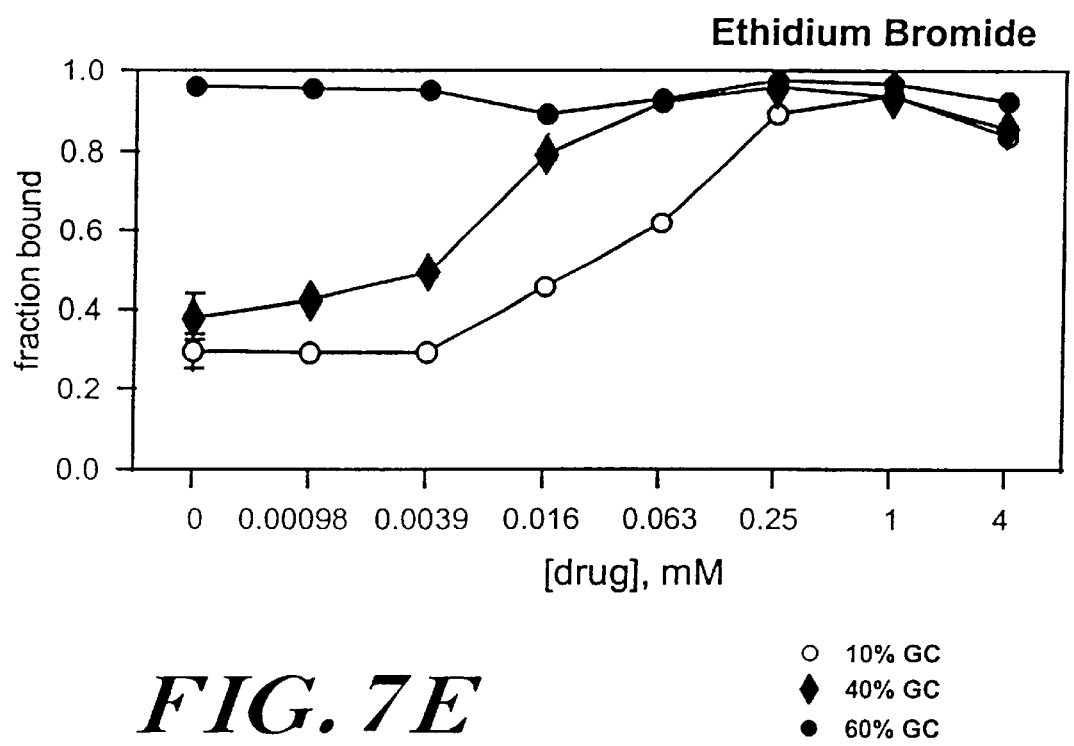

The melting profile of DNA hairpins in the presence of two base-preferring duplex-binding ligands and a nonspecific duplex denaturant is shown in FIGS. 5A and 5B. The melting curve in the presence of ethidium bromide (12:1 molar ratio of ligand to DNA), Distamycin A (1.2: molar ratio to DNA), and urea (10%) shows a marked change in shape (dashed curve) compared to the control (solid curve). The overall Tm of the hairpin mixture is only slightly altered, but the added binding ligands cause the melting transitions to divide generally into two regions: a lower melting region (below about 75° C.) and a higher melting region (above 75° C.). The amount of melting occurring in each of the two regions is not greatly altered compared to the control, but fewer duplexes melt at intermediate temperatures (between about 70° C. and 80° C.).

This experiment thus demonstrates that addition of base-preferring binding ligands can result in modulation of the melting temperatures of a plurality of duplexes.

The general applicability of the nucleic acid melting temperature normalization invention to arrays such as gene chips, for e.g., high-density hybridization studies, is demonstrated in the following Example(s). The examples study the effect of nucleic acid binding ligands and denaturants on the stability of 10-mer sequences with varying GC content bound to capture hairpins.

Test Molecules

The hairpin/target sets used are the following:

```
Set 1.
    /TTGTATAGGATCCA          CATCATCATC 5'
X   ||||||||||||||           ||||||||||
    \TTCATATCCTAGGTTGAAAAAAAAGTAGTAGTAGGACGTGTGAC 3'

Set 2.
    /TTGTATAGGATCCA          ACTTTTTTTT 5'
X   ||||||||||||||           ||||||||||
    \TTCATATCCTAGGTGTAGTAGTAGTGAAAAAAAAGACGTGTGAC 3'

Set 3.
    /TTGTATAGGATCCA          CTGCACACTG 5'
X   ||||||||||||||           ||||||||||
    \TTCATATCCTAGGTGTAGTAGTAGTGAAAAAAAAGACGTGTGAC 3'
```

X denotes biotinylated dU, and the target molecules are shown in bold face. The gap between the duplex formed by the target and the dangling end of the capture hairpin, and the duplex stem region is designed to eliminate effects to stability due to stacking with a preformed duplex. The hairpin/target duplexes shown above differ in stability because of their differences in GC content. Set 1 is 40% GC (4/10), set 2 is the least stable at 10% GC (1/10), and set 3 is most stable at 60% GC (6/10).

The ligands used were commercially available. These are:
Duplex binding ligands:
1. Actinomycin D (Sigma A-1410)
2. Distamycin A (Sigma D-6135)
3. Berenil (diminazine aceturate, Sigma D-7770)
4. bis-benzimide (Hoechst No. 33258, Sigma B-2883)
5. Ethidium bromide
6. poly(L-lysine-phenylalanine (Sigma P-3150))
7. poly(L-arginine) (Sigma P-4663)

Duplex denaturants:
8. formamide
9. urea
10. Single-Strand DNA Binding Protein (Promega M301 1)

The structures of ligands 1–5 are shown in FIG. 6.

The target molecules were labelled with $P^{32}$ following a standard kinasing protocol. The labelled bands were isolated from the reaction solutions by denaturing PAGE (8 M urea, 20% acrylamide). $P_{32}$ activity was determined by scintillation counting.

Capture Hairpin Immobilization on Microtiter Plates

A solution of the capture hairpin at 10 pmol/50 µl in PBS (150 mM NaCl, 10 mM phosphate, pH 7.2) was prepared. 50 µl/well was loaded on streptavidin-coated microtiter plates (Boehringer-Mannheim #1645692) and allowed to incubate for 30 min at room temperature. After the incubation period, the wells were washed 6 times with PBS, and blotted on clean Kimwipes.

General Procedure for Hybridization

A cocktail of the labelled targets was prepared by adding a sufficient amount of each target to the hybridization buffer to give a final concentration of ~20,000 cpm/target/50 µl. The final composition of the hybridization buffer is 1M NaCl, 10 mM phosphate, pH 7.2, and the specified concentration of the ligand. 50 µl of the target cocktail was loaded into each well, and the plate was incubated for the specified amount of time. After incubation, each reaction mixture was quantitatively transferred to a 0.2 ml tube (Costar 6547). The wells were washed once with 100 µl of hybridization buffer (without ligand) and the wash added to the tube. The tubes were sealed, and the activity was measured by Cerenkov counting.

EXAMPLE 5

DNA single-strand and duplex binding ligands were titrated into hybridization reactions using the 3 sets of molecules given above. The results of titrating ligands 1–5 are shown in FIG. 7. The hybridization reactions were carried out for 2–2.5 hours, and the ligand concentrations were changed from 0–4 mM, in 4-fold increments.

Actinomycin D acted as a single strand binder (i.e., denaturant) for the 60% GC and 10% GC content molecules. Increasing the concentration decreased the amount of target bound for these two sets of molecules. The fraction of target bound was nearly negligible at ≧0.063 mM actinomycin D. Some normalization can be seen. It is believed from this data (without wishing to be bound by this theory) that actinomycin D serves to stabilize already-formed duplexes rather than promoting, by itself, duplex formation. As such, actinomycin D may be useful in conjunction with other duplex binding ligands such as disclosed elsewhere herein.

Distamycin A is seen to stabilize duplex formation and normalize well. Even at the lowest drug concentration (0.001 mM), binding was at near completion for both the 10% GC and 40% GC.

Some normalization can be seen in the Berenil-treated samples. A stabilizing effect is seen on the 10% GC molecule; at 0.25 mM or higher, the fraction bound equaled that of the 60% GC molecule. The effect on the 40% GC molecule was more moderate.

bis-benzimide showed an effect similar to distamycin A. All three sets of duplexes were stabilized, and at ≧0.063, the hybridization is near completion. The 10% GC molecule responded to bis-benzimide even at the lowest concentration of the drug, while the 40% GC had a slower response, having a more gradual increase in its stability.

Ethidium bromide showed a more gradual effect on stability of the 10% GC and 40% GC molecules, compared to distamycin A and bisbenzimide. The 40% GC molecule also responded faster to the drug, compared to the 10% GC set. Complete hybridization occured at ≧0.25 mM ethidium bromide.

Figure 8A:
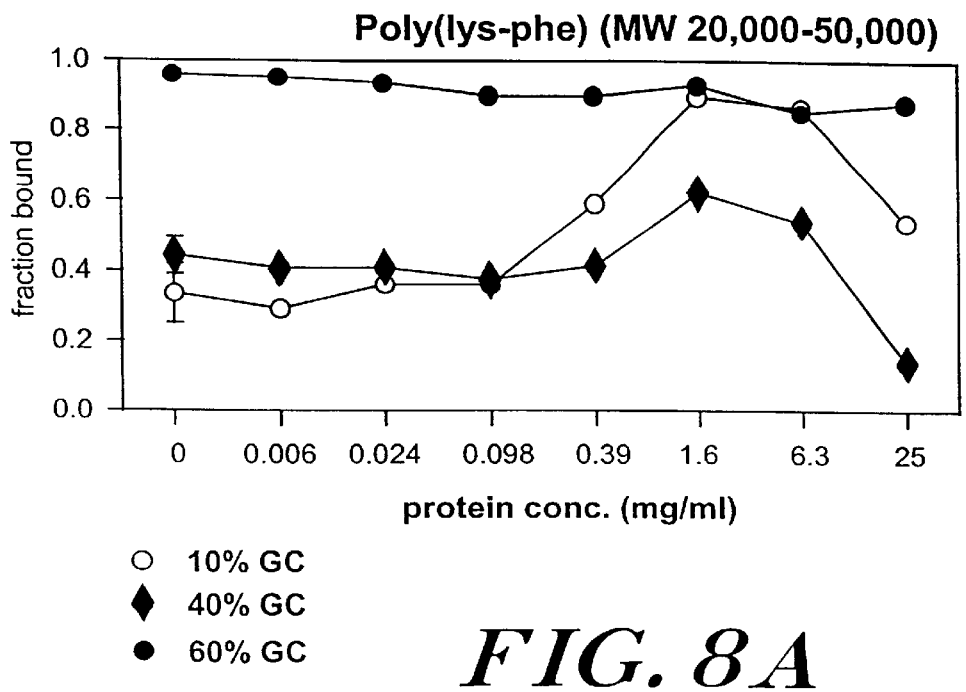
FIG. 8 shows the effect of polypeptides on hybridization as set forth in Example 5.
Figure 8B:
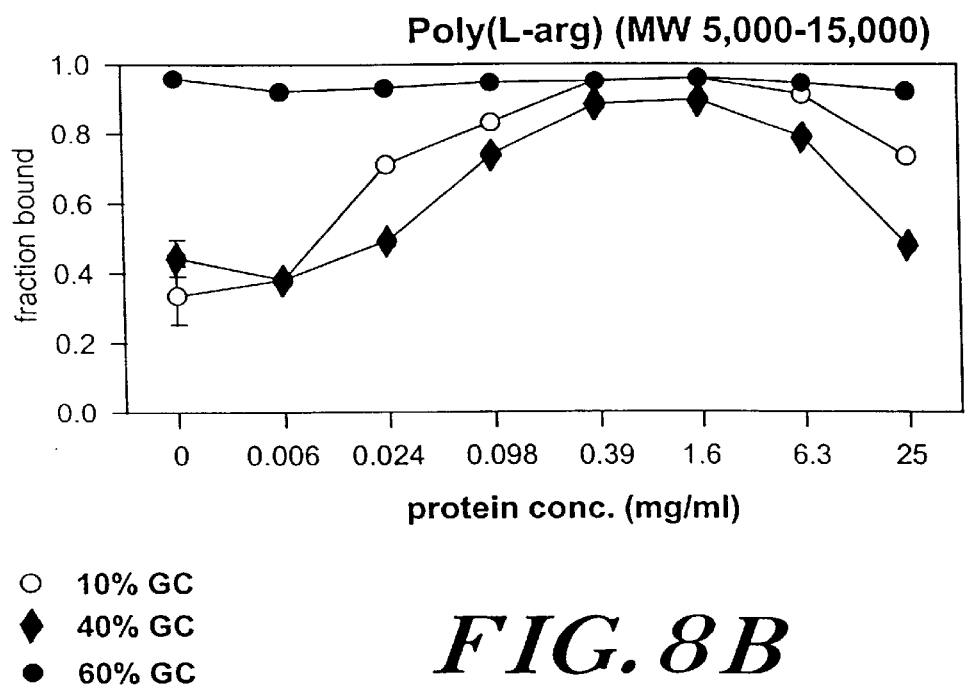

FIG. 8 shows the effect of two polypeptides on hybridization. The polypeptides were titrated into the hybridization reaction by 4-fold increments, from 0–25 mg/ml.

Poly(L-lysine-phenylalanine) affects the 10% GC molecule more than the 40% GC molecule. At 1.6–6.3 mg/ml of the protein, the fraction of the 10% GC target bound to the capture hairpin is equal to that of the 60% GC target, while fraction of the 40% GC target bound increased only to ~0.6. At >6.3% protein, both the 10% GC and 40% GC targets showed a decrease in the amount bound.

Poly(L-arginine) normalized the binding of both the 10% GC and 40% GC in a similar way. The results showed an increase in the binding of these two targets at ≧0.024 mg/ml, and at 0.4 mg/ml, the fraction bound was nearly equal to that of the 60% GC target. At >1.6 mg/ml, there was a decrease in the fraction of the 10% GC and 40% GC targets bound.

EXAMPLE 6

Target/Capture Hairpin Association Rates

Three drugs were chosen for experiments to determine their effects on duplex association rates, the control of which is also beneficial in the application of the present invention to gene chips, e.g., to increase assay speed and/or throughput in applications such as high density nucleic acid arrays. In these experiments, distamycin A, berenil, and bisbenzimide were each kept constant at 1 mM. Samples were obtained at different incubation times and the amount of target bound was measured.

FIG. 9 shows the effect of distamycin A on the association rates of the three sets of target/hairpin molecules. Without distamycin A (left panel), binding of the 40% GC and 10% GC molecules went up to ~60% by 80 minutes, while the binding of the 60% GC set went up to >90%. With distamycin A (right panel), binding of all three molecules were up to >90% by 80 minutes.

FIG. 10 shows a similar study using berenil, this time using only the 60% GC and 10% GC molecules. Without the ligand (left panel), the 10% GC set showed a low binding affinity to the hairpin (at ~40% at 2 hours). With the ligand, the binding curves of both molecules were similar. The binding curve of the 60% GC target was pulled down, with ~70% binding after 2 hours. However, the binding curve of the 10% GC target was pulled up, to ~75% binding after 2 hours.

Figure 11B:
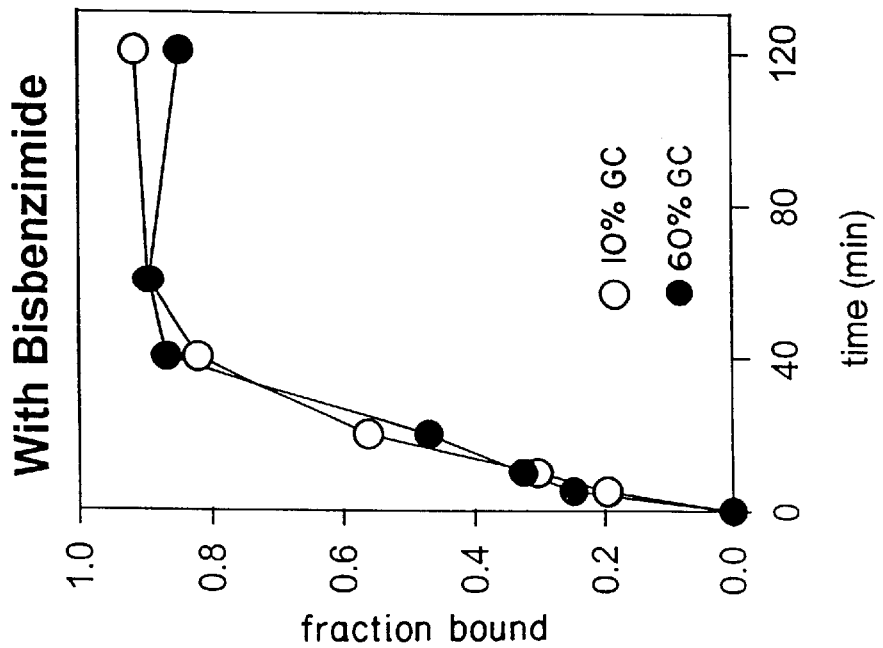
FIG. 11 shows the effect of bisbenzamide on the association rates of the three sets of target/hairpin molecules, as set forth in Example 6.
Figure 11A:
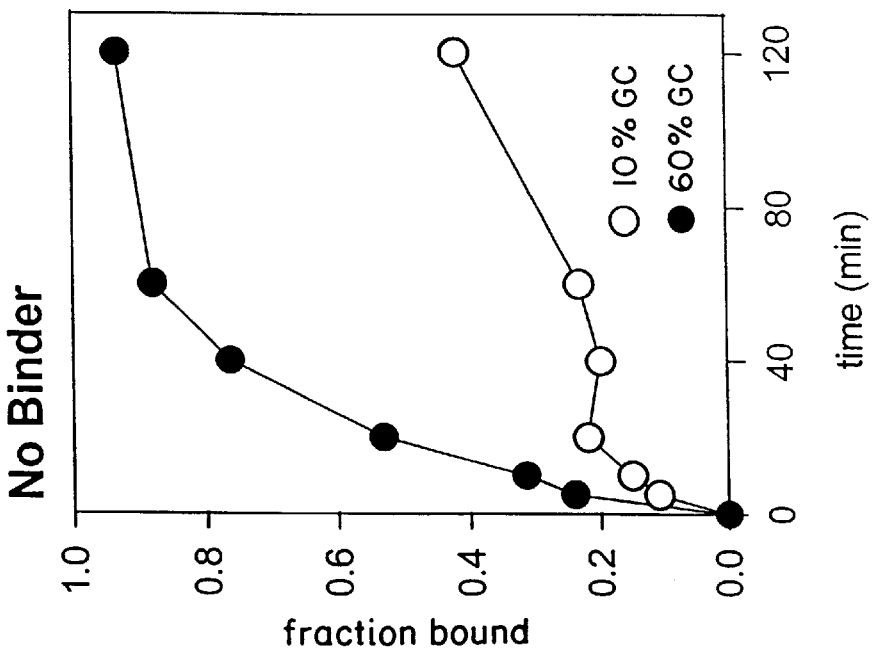

FIG. 11 shows the effect of bisbenzimide on the 60% GC and 10% GC molecules. The "no ligand" experiment is the same as the one shown in FIG. 10. With bisbenzimide, both sets were pulled up, with similar binding profiles. Binding was at ~90% for both molecules at 40 minutes.

EXAMPLE 7

Hybridization with Duplex Denaturants

Figure 12A:
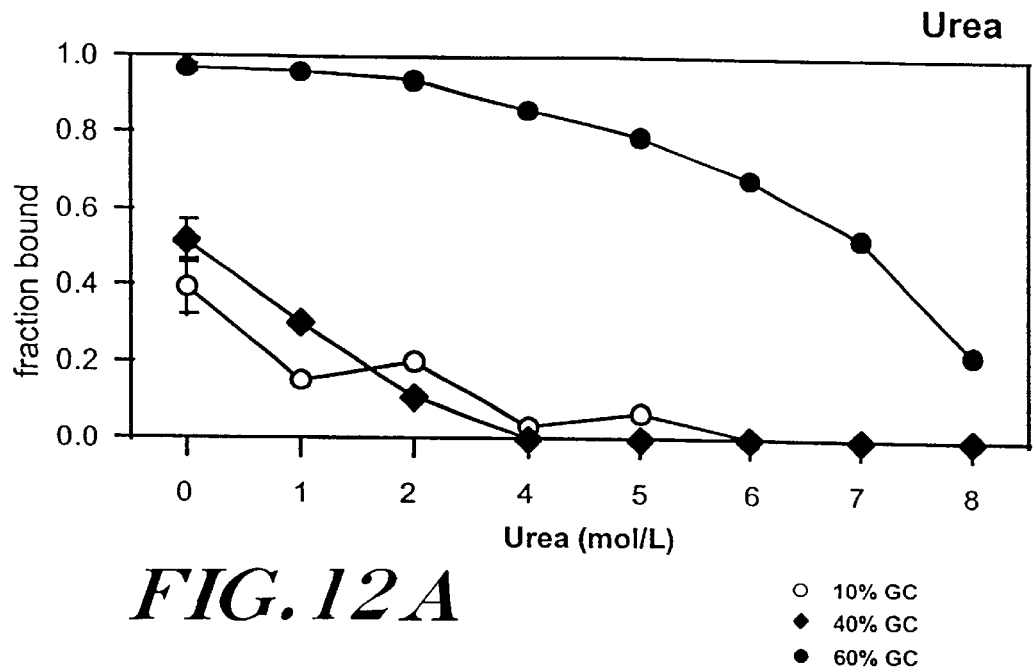
FIG. 12 shows results of titration of the hairpin/target sets with various duplex denaturants, as shown in Example 7.
Figure 12B:
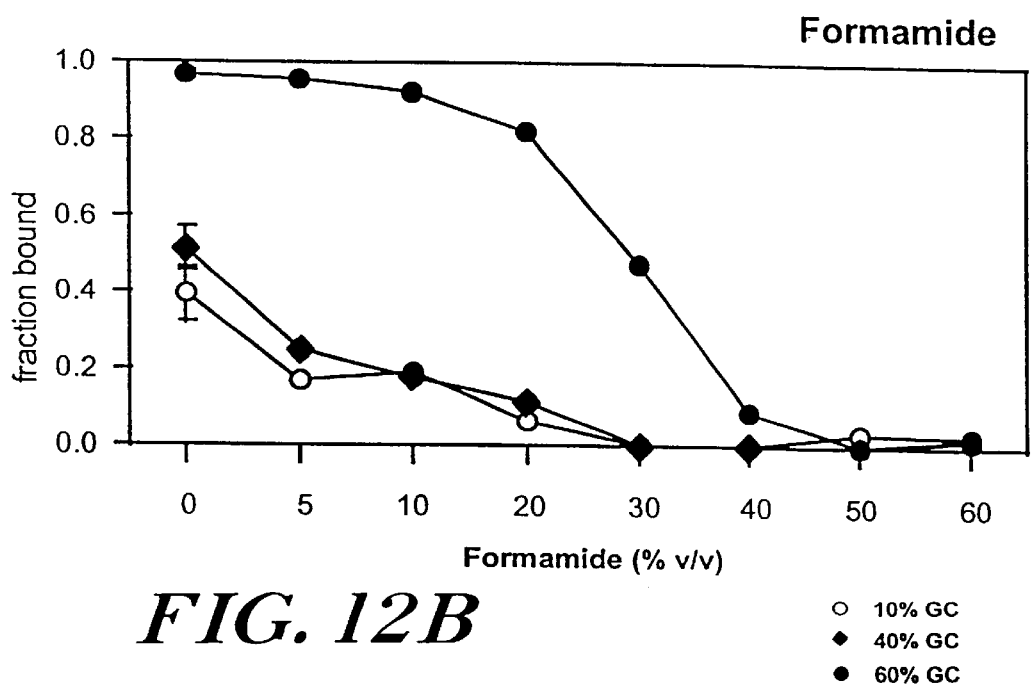
Figure 12C:
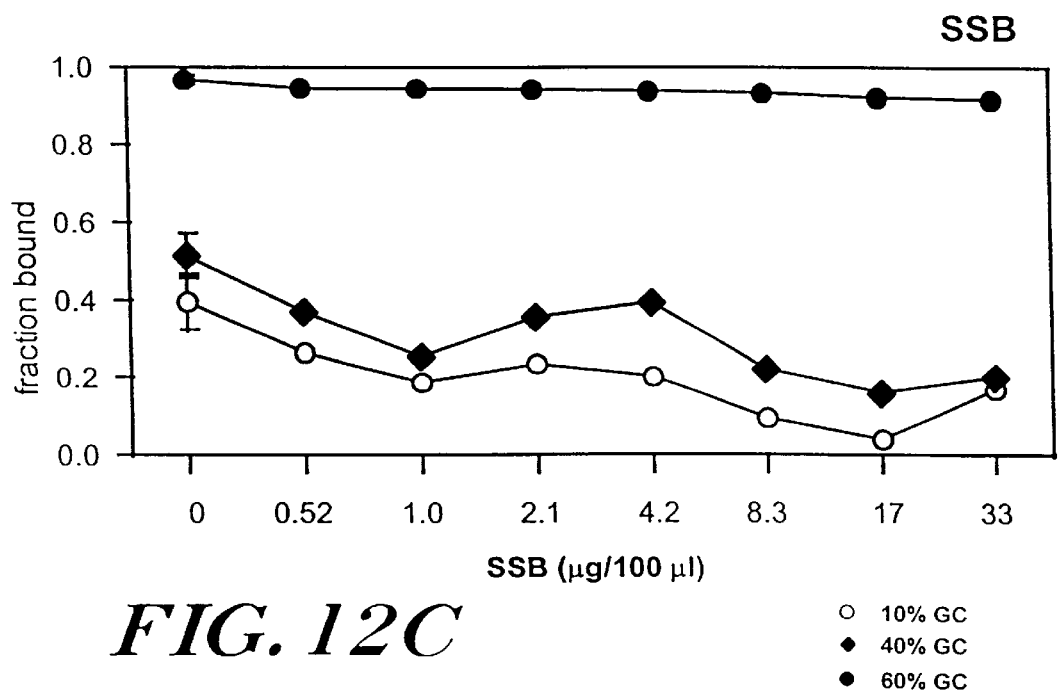

To illustrate and determine the effect and relative selectivity of certain denaturants with respect to GC content, experiments were performed wherein the target molecules were hybridized to their respective capture hairpins with denaturants titrated in. The buffer was kept constant at 1M NaCl, 10 mM phosphate, pH 7.2, and the hybridization time was between 2–2.5 hours. The following denaturants were used: urea, formamide, and single strand DNA binding protein (SSB). The results are shown in FIG. 12.

The effect of urea on the 60% GC target was gradual. Binding was significantly decreased at a concentration of ≧4 M, and there is still some binding (~20%) at 8 M. The 40% GC and 10% GC molecules were more affected, and no significant binding was measured at ≧4 M urea.

Formamide showed a similar effect on the 40% GC and 10% GC target molecules. Binding of the two molecules went down to ~10% at 20% (v/v) formamide, and at 30% or more formamide, binding was insignificant. The 60% GC target was affected more gradually, with binding reduced to ~50% at 30% (v/v) formamide, with almost no binding at ≧40% formamide.

SSB had no effect on the binding of the 60% GC target under the above hybridization conditions. The effect on the 40% GC and 10% GC is more gradual, with no apparent decrease in the amount of target bound up to a concentration of >8.3 mg/ml of SSB.

From the data it can be seen that a duplex denaturant and a concentration therefor, may be selected for use after hybridization and normalization to selectively remove mismatched hybridizations.

Those skilled in the art will recognize, or be able to ascertain using no more than routine experimentation, numerous equivalents to the specific procedures described herein. Such equivalents are considered to be within the scope of this invention and are covered by the following claims.

The contents of all references and patent applications described herein are hereby incorporated by reference.

Other embodiments are within the following claims.

What is claimed is:

1. A method of hybridization of at least two nucleic acid duplexes to a nucleic acid target, wherein said method comprises:

contacting said at least two nucleic acid duplexes with a reaction mixture comprising a nucleic acid binding ligand which preferentially binds to one of the at least two nucleic acid duplexes such that the melting temperatures of the at least two nucleic acid duplexes are normalized; and hybridizing said at least two nucleic acid duplexes to said nucleic acid target.

2. The method of claim 1, wherein the nucleic acid binding ligand is a duplex-binding ligand.

3. The method of claim 2, wherein the duplex-binding ligand is distamycin.

4. The method of claim 1, wherein the reaction mixture comprises at least two nucleic acid binding ligands, and wherein each of the at least two nucleic acid binding ligands independently binds preferentially to one of the at least two nucleic acid duplexes.

5. The method of claim 4, wherein the reaction mixture comprises at least two duplex-binding ligands.

6. The method of claim 4, wherein at least one of the at least two nucleic acid binding ligands is a single-strand-binding ligand.

7. The method of claim 1, wherein the reaction mixture further comprises at least one nonspecific binding ligand.

8. The method of claim 1, wherein the reaction mixture further comprises a duplex denaturant.

9. The method of claim 8, wherein the duplex denaturant is urea.

10. A method of hybridizing a plurality of nucleic acid duplexes to a nucleic acid target, the method comprising:

(i) providing said plurality of nucleic acid duplexes;

(ii) forming a reaction mixture comprising said plurality of nucleic acid duplexes and a base-preferring nucleic acid binding ligand such that the melting temperatures of said plurality of nucleic acid duplexes are normalized; and (iii) hybridizing said plurality of nucleic acid duplexes to said nucleic acid target.

11. The method of claim 10, wherein the base-preferring binding ligand is a duplex-binding ligand.

12. The method of claim 11, wherein the reaction mixture further comprises a single-strand-binding ligand.

13. The method of claim 10, wherein the reaction mixture comprises at least two nucleic acid binding ligands, and wherein each of the at least two nucleic acid binding ligands independently binds preferentially to one of the at least two nucleic acid duplexes.

14. The method of claim 10, wherein at least one of the at least two nucleic acid binding ligands is a single-strand-binding ligand.

15. The method of claim 10, wherein the reaction mixture comprises at least two duplex-binding ligands.

16. The method of claim 10, wherein the reaction mixture further comprises at least one nonspecific binding ligand.

17. The method of claim 10, wherein the reaction mixture further comprises a duplex denaturant.

18. The method of claim 17, wherein the duplex denaturant is urea.

19. A hybridization buffer for normalizing melting temperatures of at least two nucleic acid duplexes, the buffer comprising:
 a duplex denaturant; and
 a base-preferring nucleic acid binding ligand in an amount effective to normalize melting temperatures of at least two nucleic acid duplexes.

20. The buffer of claim 19, wherein the base-preferring binding ligand is a duplex-binding ligand.

21. The buffer of claim 19, wherein the buffer further comprises a single-strand-binding ligand.

22. The buffer of claim 19, wherein the buffer comprises at least two nucleic acid binding ligands, and wherein each of the at least two nucleic acid binding ligands independently binds preferentially to one of the at least two nucleic acid duplexes.

23. The buffer of claim 22, wherein at least one of the at least two nucleic acid binding ligands is a single-strand-binding ligand.

24. The buffer of claim 19, wherein the reaction mixture comprises at least two duplex-binding ligands.

25. The buffer of claim 19, wherein a reaction mixture further comprises at least one nonspecific binding ligand.

26. The buffer of claim 19, wherein the reaction mixture further comprises a duplex denaturant.

27. The buffer of claim 26, wherein the duplex denaturant is urea.

28. A method of determining the sequence of a nucleic acid target, comprising:
 a) providing said nucleic acid target;
 b) providing a plurality of immobilized nucleic acid capture moieties;
 c) cleaving said nucleic acid target into a nested set of nucleic acid fragments;
 d) forming a reaction mixture comprising said immobilized nucleic acid capture moieties, said nested set of nucleic acid fragments, and at least one base-preferring nucleic acid binding ligand under conditions such that at least one nucleic acid fragment will hybridize to at least one nucleic acid capture moiety to form at least one duplex, wherein the melting temperatures of said nested set of nucleic acid fragments are normalized;
 e) detecting those nucleic acid capture moieties which have hybridized to a target nucleic acid fragment; and
 f) determining the sequence of the nucleic acid target by compiling the overlapping sequences of the bound fragments.

29. The method of claim 28, wherein the reaction mixture is formed under conditions such that the at least one base-preferring nucleic acid binding ligand can modulate the stability of at least one duplex.

30. A method of determining the sequence of a nucleic acid target, comprising:
 a) providing said nucleic acid target;
 b) providing a plurality of immobilized nucleic acid capture moieties;
 c) forming a reaction mixture comprising said immobilized nucleic acid capture moieties, said nucleic acid target, and at least one base-preferring nucleic acid binding ligand under conditions such that the nucleic acid target will hybridize to at least one nucleic acid capture moiety to form at least one duplex, wherein the melting temperatures of said nucleic acid target is normalized;
 d) detecting those nucleic acid capture moieties which have hybridized to the nucleic acid target; and
 e) determining the sequence of the nucleic acid target by compiling the overlapping sequences of those nucleic acid capture moieties which have hybridized to the nucleic acid target.

31. The method of claim 30, wherein the reaction mixture is formed under conditions such that the at least one base-preferring nucleic acid binding ligand can modulate the stability of at least one duplex.

32. A method of hybridizing a plurality of nucleic acid duplexes to a nucleic acid target, the method comprising:
 (i) providing said plurality of nucleic acid duplexes in an array;
 (ii) forming a reaction mixture comprising said plurality of nucleic acid duplexes and a base-preferring nucleic acid binding ligand such that the melting temperatures of said plurality of nucleic acid duplexes are normalized; and
 (iii) hybridizing said plurality of nucleic acid duplexes to said nucleic acid target.

33. The method of claim 32, wherein the base-preferring binding ligand is a duplex-binding ligand.

34. The method of claim 33, wherein the reaction mixture further comprises a single-strand-binding ligand.

35. The method of claim 32, wherein the reaction mixture comprises at least two nucleic acid binding ligands, and wherein each of the at least two nucleic acid binding ligands independently binds preferentially to one of the at least two nucleic acid duplexes.

36. The method of claim 35, wherein at least one of the at least two nucleic acid binding ligands is a single-strand-binding ligand.

37. The method of claim 32, wherein the reaction mixture comprises at least two duplex-binding ligands.

38. The method of claim 32, wherein the reaction mixture further comprises at least one nonspecific binding ligand.

39. The method of claim 32, wherein the reaction mixture further comprises a duplex denaturant.

40. The method of claim 32, wherein the duplex denaturant is selected from the group consisting of urea, formamide, single strand DNA binding protein, and polypeptides.

41. The method of claim 33 wherein said duplex binding ligand is selected from the group consisting of actinomycin D, distamycin A, berenil, bis-benzamide, and ethidium bromide.

42. The method of claim 11 wherein said duplex binding ligand is selected from the group consisting of actinomycin D, distamycin A, berenil, bis-benzamide, and ethidium bromide.

* * * * *